United States Patent
Tsuchiya et al.

(10) Patent No.: US 9,046,516 B2
(45) Date of Patent: Jun. 2, 2015

(54) IMMUNOASSAY METHOD, REAGENT KIT FOR DETECTING ALKALINE PHOSPHATASE, AND REAGENT KIT FOR IMMUNOASSAY

(75) Inventors: Hiroshi Tsuchiya, Kobe (JP); Takuya Odawara, Kakogawa (JP)

(73) Assignee: SYSMEX CORPORATION, Kobe-shi (JP)

( * ) Notice: Subject to any disclaimer, the term of this patent is extended or adjusted under 35 U.S.C. 154(b) by 0 days.

(21) Appl. No.: 12/062,170

(22) Filed: Apr. 3, 2008

(65) Prior Publication Data

US 2008/0254492 A1 Oct. 16, 2008

(30) Foreign Application Priority Data

Apr. 3, 2007 (JP) ................................ 2007-096980
Feb. 29, 2008 (JP) ................................ 2008-051309

(51) Int. Cl.
*G01N 33/53* (2006.01)
*G01N 33/543* (2006.01)
*G01N 33/573* (2006.01)
*G01N 33/58* (2006.01)

(52) U.S. Cl.
CPC ........ *G01N 33/54393* (2013.01); *G01N 33/573* (2013.01); *G01N 33/581* (2013.01)

(58) Field of Classification Search
CPC .............. C12Q 1/6886; C12Q 1/6837; G01N 33/5011; G01N 27/745; G01N 24/08; G01N 33/57419; G01N 33/5008; G01N 33/5023; G01N 33/5091; G01N 33/57415; G01N 2550/00; G01N 2800/52; G01N 33/54326
See application file for complete search history.

(56) References Cited

U.S. PATENT DOCUMENTS

| | | | |
|---|---|---|---|
| 5,093,231 A | | 3/1992 | Hoke |
| 5,094,939 A | * | 3/1992 | Okada et al. ........................ 435/6 |
| 5,279,935 A | * | 1/1994 | Nycz ................................. 435/5 |
| 5,516,647 A | * | 5/1996 | Husain et al. .................... 435/21 |
| 5,587,240 A | * | 12/1996 | Kobayashi et al. ............ 428/367 |
| 5,939,038 A | * | 8/1999 | Wilkomirsky ................ 423/276 |
| 5,948,630 A | * | 9/1999 | Singh et al. ...................... 435/21 |

FOREIGN PATENT DOCUMENTS

| | | |
|---|---|---|
| EP | 0369362 A | 5/1990 |
| EP | 0 530 490 A1 | 3/1993 |
| EP | 0530490 A | 3/1993 |
| JP | 2001-183374 A | 6/2001 |

OTHER PUBLICATIONS

Dickinson et al., (The Analyst, 1971; vol. 96 pp. 248-253).*
Applied Biosystems Application (2001, retrieved from URL:www.blossombio.com/pdf/products/UG_CDP-star_CSPD.pdf).*
Morris R E et al Cellular Enzyme Linked Immuno Specific Assay 4. Inhibition of Endogenous Cellular Alkaline Phosphatase Activity, Journal of Immunological Methods vol. 68, No. 1-2, 1984 p. 11-18.
Hanson K A et al the Effect of PH and Temperature on Levamisole Stability in Aqueous Solution, Federation Proceedings vol. 42, No. 4 1983, pg Abstract 3865 & 67th Annual Meeting of the Federation of American Societies for Experimental Biology, Chicago, Ill.

* cited by examiner

*Primary Examiner* — Shafiqul Haq
*Assistant Examiner* — Carmencita M Belei
(74) *Attorney, Agent, or Firm* — Sughrue Mion, PLLC

(57) ABSTRACT

An immunoassay method comprising:
forming, on a solid phase, a complex comprising a measurement substance in a sample, an alkaline phosphatase (ALP) labeling substance capable of binding to the measurement substance, and a first binding substance which is capable of binding to the measurement substance by antigen-antibody reaction and is capable of binding to the solid phase;
reacting ALP in the ALP-labeling substance bound to the measurement substance in the complex, with a substrate for ALP contained in a substrate solution, in the presence of an auxiliary reagent solution comprising an inhibitor for inhibiting an endogenous ALP; and
detecting a reaction product produced by the reaction between ALP and the substrate.

13 Claims, 2 Drawing Sheets

FIG.4

IMMUNOASSAY METHOD, REAGENT KIT FOR DETECTING ALKALINE PHOSPHATASE, AND REAGENT KIT FOR IMMUNOASSAY

FIELD OF THE INVENTION

The present invention relates to an immunoassay method using the reagent kit for immunoassay, a reagent kit for alkaline phosphatase, and a reagent kit for immunoassay.

BACKGROUND

An alkaline phosphatase (also referred to hereinafter as ALP) is an enzyme used generally as a label in enzyme immunoassay. ALP can be seen in almost all living things ranging from higher animals to bacteria, and in higher animals, there are organ-specific isozymes. It is known that a body fluid such as blood contains endogenous ALP such as liver-derived ALP and bone-derived ALP. Therefore, in the case of immunoassay with ALP as a label, not only an ALP label but also an endogenous ALP derived from a sample reacts with a substrate, thus sometimes failing to attain accurate measurement results.

As a substance useful for suppressing the influence of such endogenous ALP, there is an inhibitor of endogenous ALP. Methods of using an inhibitor of endogenous ALP for suppressing the influence of endogenous ALP are as follows:

U.S. Pat. No. 5,948,630 describes a method of reducing the influence of endogenous ALP, which comprises using a detergent composition containing an inhibitor of human ALP.

EP Publication No. 530490 describes a method which comprises labeling, with ALP, an antibody binding to a cell surface marker such as CD4, and using the ALP-labeled antibody to classify the subtype of a lymphocyte. In this method, a substrate-containing substrate solution/buffer, pH 9.5, and a levamisole-containing cell wash fluid, pH 7.4, are used.

In U.S. Pat. No. 5,948,630, a substrate/wash fluid containing 4-MUP as a substrate and levamisole as an inhibitor of endogenous ALP is used in the Examples. The optimum pH of ALP is alkaline, so in general, reagents including its substrate are set alkaline so that the ALP label can react under the preferable conditions with the substrate. In U.S. Pat. No. 5,948,630, it is described that the pH of the detergent composition is preferably in the range of about 7.0 to 10.0. However, the inhibitor of endogenous ALP such as levamisole is destabilized at alkaline pH. In the detergent composition described in U.S. Pat. No. 5,948,630, therefore, the inhibitor of endogenous ALP cannot be used in a stabilized state in some cases.

In EP Publication No. 530490, cells treated with an ALP-labeled antibody are washed twice with the cell wash fluid, and then the substrate solution/buffer is added to measure staining with ALP activity. Generally, the cell wash fluid is removed from the cells after washing, and thus a reaction solution where the ALP label is reacted with the substrate is substantially free of the cell wash fluid. Accordingly, if endogenous ALP cannot be sufficiently inhibited at the time of washing, there is a possibility that the influence of the endogenous ALP cannot be completely eliminated at the time of the reaction between the ALP label and the substrate.

SUMMARY OF THE INVENTION

The scope of the present invention is defined solely by the appended claims, and is not affected to any degree by the statements within this summary.

A first aspect of the present invention is an immunoassay method comprising: forming, on a solid phase, a complex comprising a measurement substance in a sample, an alkaline phosphatase (ALP) labeling substance capable of binding to the measurement substance, and a first binding substance which is capable of binding to the measurement substance by antigen-antibody reaction and is capable of binding to the solid phase; reacting ALP in the ALP-labeling substance bound to the measurement substance in the complex, with a substrate for ALP contained in a substrate solution, in the presence of an auxiliary reagent solution comprising an inhibitor for inhibiting an endogenous ALP; and detecting a reaction product produced by the reaction between ALP and the substrate.

A second aspect of the present invention is an immunoassay method comprising: mixing a sample, an alkaline phosphatase (ALP) labeling substance, a first binding substance capable of binding to the ALP-labeling substance and a measurement substance in the sample by antigen-antibody reaction, and a solid phase for supporting the first binding substance; reacting ALP of the ALP-labeling substance bound to the first binding substance supported by a solid phase, with a substrate for ALP contained in a substrate solution, in the presence of an auxiliary reagent solution comprising an inhibitor for inhibiting an endogenous ALP; and detecting a reaction product produced by the reaction between ALP and the substrate.

A third aspect of the present invention is a reagent kit for detecting alkaline phosphatase (ALP) comprising: an ALP-labeling substance capable of binding to a target substance; a substrate solution comprising a substrate for ALP; an auxiliary reagent solution comprising an inhibitor for inhibiting an endogenous ALP and which is added at the time of the reaction between ALP in the ALP-labeling substance bound to the target substance and the substrate.

A fourth aspect of the present invention is a reagent kit for immunoassay comprising: a first binding substance capable of binding to a measurement substance by antigen-antibody reaction; a solid phase for supporting a complex comprising the measurement substance and the first binding substance; an alkaline phosphatase (ALP) labeling substance capable of binding to the measurement substance of the complex; a substrate solution comprising a substrate for ALP; and an auxiliary reagent solution comprising an inhibitor for inhibiting an endogenous ALP and which is added at the time of reaction between ALP in the ALP-labeling substance bound to the measurement substance of the complex and the substrate.

A fifth aspect of the present invention is a reagent kit for immunoassay comprising: an alkaline phosphatase (ALP) labeling substance; a first binding substance capable of binding to a measurement substance and the ALP-labeling substance by antigen-antibody reaction; a solid phase for supporting the first binding substance; a substrate solution comprising a substrate for ALP; and an auxiliary reagent solution comprising an inhibitor for inhibiting an endogenous ALP and which is added at the time of reaction between ALP in the ALP-labeling substance bound to the first binding substance and the substrate.

DETAILED DESCRIPTION OF THE PREFERRED EMBODIMENTS

The preferred embodiments of the present invention are described hereinafter with reference to the drawings.
Reagent Kit for Detecting ALP In this specification, the "reagent kit for detecting ALP" is a reagent kit comprising an ALP-labeling substance capable of binding to the target substance, a substrate solution containing a substrate for ALP, and an auxiliary reagent solution containing an inhibitor for inhibiting an endogenous ALP and which is added at the time of the reaction between ALP bound to the target substance and the substrate, and is used for detecting ALP.

In this specification, the "auxiliary reagent solution" contained in the reagent kit for detecting ALP is a reagent added when an ALP label is reacted with a substrate. In the reagent kit for detecting ALP, the auxiliary reagent solution is provided as a reagent different from the substrate solution. The auxiliary reagent solution may be added when ALP is reacted with a substrate, and which can be used for a particle dispersion allowing the particles having an ALP label in a dispersed state in a liquid phase to be contacted with the substrate.

In this specification, "contact" includes mixing.
Reagent Kit for Immunoassay

The reagent kit for detecting ALP may be formed into a reagent kit for immunoassay used for immunoassay with a solid phase.

The reagent kit for immunoassay in this embodiment is a reagent kit for detecting ALP used in solid phase immunoassay. The solid phase immunoassay includes immunoassay using a sandwich method and immunoassay using a competitive method. Now, these measurement methods are briefly described.

In this specification, when an immunoassay is carried out by sandwich method, "a first binding substance" is a substance capable of binding to a measurement substance in a sample by antigen-antibody reaction, and capable of binding to a solid phase. In this specification, when an immunoassay is carried out by competitive method, "a first binding substance" is a substance capable of binding to a measurement substance in a sample and the ALP-labeling substance by antigen-antibody reaction, and capable of binding to a solid phase.

In this specification, "a free first binding substance" is the first binding substance which did not form a complex containing the measurement substance, in other words, which did not bind to the measurement substance in a sample, among the first binding substance obtained by mixing a sample, a first binding substance and a solid phase.

The solid phase immunoassay includes a step of contacting a measurement substance, a first binding substance binding to the measurement substance by an antigen-antibody reaction, and a solid phase with one another to form, on the solid phase, a complex containing at least the measurement substance and the first binding substance. Generally, the complex is supported on the solid phase by immobilizing the first binding substance on the solid phase. Not only the complex, but also the free first binding substance is supported on the solid phase.

In the sandwich method, the complex among the substances (that is, the complex and the free first binding substance) supported on the solid phase is labeled, and on the basis of the detection result of this label, the measurement substance is measured.

In the competitive method, on the other hand, the free first binding substance among the substances (the complex and the free first binding substance) supported on the solid phase is labeled, and on the basis of the detection result of this label, the measurement substance is measured.

The first binding substance is not particularly limited insofar as it binds to the measurement substance by an antigen-antibody reaction. For example, when the measurement substance is an antibody, the first binding substance includes an antigen binding specifically to the antibody. The antigen as the first binding substance is not particularly limited insofar as it has a site (epitope) recognized by the antibody that is the measurement substance.

When the measurement substance is an antigen, the first binding substance includes an antibody binding specifically to the antigen. The antibody as the first binding substance is not particularly limited insofar as it is an antibody binding specifically to the antigen that is the measurement substance, and the first binding substance includes a fragment of the antibody and derivative thereof.

Specific examples include Fab fragments, F(ab') fragments, F(ab)2 fragments, and sFv fragments. The antibody class to be used includes, but is not limited to, IgG and IgM.

The complex is not particularly limited insofar as in the solid phase immunoassay, it is a complex formed on a solid phase and containing at least the measurement substance and the first binding substance. For example, when a primary antibody binding to the measurement substance, and a labeled secondary antibody binding to the primary antibody are used to label the complex, the complex can contain the measurement sample, the first binding substance and the primary antibody.

The ALP-labeling substance comprises a second binding substance capable of binding to the target substance, and ALP.

The target substance is a substance which is labeled by ALP. In the case of the sandwich method, the target substance is the measurement substance in the complex formed by the measurement substance and the first binding substance, in the case of the competitive method, the target substance is the free first binding substance.

In the case of the sandwich method, the ALP-labeling substance is obtained by labeling, with ALP, a second binding substance capable of binding to the complex among the complex and the free first binding substance on the solid phase. In the case of the competitive method, the ALP-labeling substance is obtained by labeling, with ALP, a second binding substance capable of binding to the free first binding substance among the complex and the free first binding substance on the solid phase.

The second binding substance is not particularly limited insofar as it can be used in immunoassay, and the second binding substance can be suitably selected depending on the type of the measurement substance and the measurement method.

For example, when the measurement substance is an antigen in immunoassay using the sandwich method, the second binding substance is a substance binding directly or indirectly to the antigen as the measurement substance.

The second binding substance binding directly to the antigen may be an antibody binding specifically to the antigen. The antibody is not particularly limited insofar as it is an antibody binding specifically to an antigen as the measurement substance, and the antibody also includes an antibody fragment and its derivative. Specific examples include Fab fragments, F(ab') fragments, F(ab)2 fragments, and sFv fragments. The antibody class used includes, but is not limited to, IgG and IgM. In this case, the antibody as the first binding substance and the antibody as the second binding substance are preferably those recognizing different sites (epitopes) of the antigen.

The second binding substance binding indirectly to an antigen as the measurement substance may be a secondary antibody capable of binding to a primary antibody binding specifically to the antigen. In this case, the secondary antibody can bind to the measurement substance via a primary antibody. Examples of the secondary antibody include, for example, antibodies such as IgG, IgM and IgY to human antibodies. When biotin is added to the primary antibody, avidin or the like can be used as the second binding substance in place of the secondary antibody.

The primary antibody is not particularly limited insofar as it is an antibody binding specifically to an antigen as the measurement substance, and the primary antibody also includes an antibody fragment and its derivative. In this case, the antibody as the first binding substance and the primary antibody as the second binding substance are preferably those recognizing different sites (epitopes) of the antigen. The second antibody is not particularly limited insofar as it is an antibody binding to the primary antibody, and the second antibody also includes an antibody fragment and its derivative.

When the measurement substance in the immunoassay using the sandwich method is an antibody, the second binding substance is a substance capable of binding to an antibody as the measurement substance. Such second binding substance may be an antibody or antigen capable of binding to an antibody. The antibody as the second binding substance includes antibodies such as IgG, IgM and IgY to human antibodies.

When the measurement substance in the immunoassay using the competitive method is an antigen, the second binding substance is a substance capable of binding to an antibody as the first binding substance immobilized on a solid phase. Specifically, an antigen capable of binding to an antibody as the first binding substance can be used. The antigen as the second binding substance is not particularly limited insofar as it has a site (epitope) recognized by the antibody as the first binding substance.

When the measurement substance in the immunoassay using the competitive method is an antibody, the second binding substance is a substance capable of binding to an antigen as the first binding substance immobilized on a solid phase. Specifically, an antibody capable of binding to an antigen as the first binding substance can be used. The antibody as the second binding substance is not particularly limited insofar as it is an antibody binding specifically to an antigen as the first binding substance, and the antibody also includes an antibody fragment and its derivative.

The ALP used as a label is not particularly limited insofar as it is not inhibited by an inhibitor of endogenous ALP contained in the auxiliary reagent solution. Examples of such ALP include intestine-derived ALP, bacterium-derived ALP, etc. The intestine-derived ALP includes, for example, bovine intestine-derived ALP, etc. The bacterium-derived ALP includes, for example, *Escherichia coli*-derived ALP, yeast-derived ALP, etc. From the viewpoint of specific activity and productivity, the intestine-derived ALP is preferably used. ALP used as a label may be isolated from nature or may be synthesized by methods known in the art, such as genetic recombination methods and chemical synthesis methods.

The optimum pH of ALP used as the label varies depending on its type; for example, the optimum pH of intestine-derived ALP is pH 9 to 10 or so, and the optimum pH of bacterium-derived ALP is pH 8 to 9 or so.

The method of labeling the second binding substance with ALP may be a known method. The method of labeling it with ALP includes, for example, a glutaraldehyde method, a periodic acid crosslinking method, a maleimide crosslinking method, a carbodiimide method, an activated ester method etc.

In the reagent kit for immunoassay, the ALP-labeling substance may be in the form of a liquid dissolved in a buffer solution or in the form of a solid obtained by lyophilization and used by adding a liquid such as water just before use. From the viewpoint of ease in using and handling the reagent kit, the ALP-labeling substance is preferably in the form of a liquid dissolved in a buffer solution.

The auxiliary reagent solution is used in solid phase immunoassay, contains an inhibitor for inhibiting an endogenous ALP (also referred to hereinafter as an inhibitor of endogenous ALP), and is added at the time of the reaction between ALP in the solid phase on which the ALP-labeling substance-bound complex is supported and the substrate.

The auxiliary reagent solution is used in solid phase immunoassay using the competitive method, contains an inhibitor of endogenous ALP, and is added at the time of the reaction between ALP in the solid phase on which the ALP-labeling substance-bound first binding substance is supported and the substrate.

That is, the auxiliary reagent solution is a reagent containing an inhibitor of endogenous ALP and added at the time of the reaction between the ALP label on a solid phase and the substrate in solid phase immunoassay. The auxiliary reagent solution may be a solution added at the time of the reaction between the ALP label on a solid phase and the substrate, and for example when particles are used as a solid phase, the reagent can be used as a particle dispersion for allowing the particles having an ALP label in a dispersed state in a liquid phase to be contacted with the substrate.

The inhibitor of endogenous ALP is not particularly limited insofar as it does not inhibit labeling ALP but inhibits endogenous ALP derived from a sample. A typical inhibitor of endogenous ALP includes levamisole. Levamisole is chemically (−)-2,3,5,6-tetrahydro-6-phenylimidazo[1,2-b]thiazole. Many homologues of levamisole are known, and these homologues can also be used as inhibitors of endogenous ALP. Such homologues include, for example, homologues of levamisole whose phenyl ring is substituted with a C1 to C6 lower alkyl group and homologues of levamisole whose phenyl ring is substituted with a halogen atom such as chlorine or bromine. Further, tetramisole that is a racemate of levamisole can also be used as an inhibitor of endogenous ALP. Such homologues can be exemplified by tetramisole and L-p-bromotetramisole. Other examples of the inhibitor of endogenous ALP include 5,6-dihydro-6-(2-naphthyl)imidazo-[2,1-b]thiazole.

It is known that the inhibitor of endogenous ALP is destabilized at alkaline pH. Therefore, from the viewpoint of the storage stability of the inhibitor of endogenous ALP in the reagent, the auxiliary reagent solution preferably has pH at which the inhibitor of endogenous ALP is stable. Preferably, the pH of the auxiliary reagent solution is for example neutral or acidic. Specifically, the pH of the auxiliary reagent solution is preferably pH 4 to 8, more preferably pH 6 to 7.

In the reagent kit for immunoassy, the substrate solution can be at alkaline pH optimum for an ALP label. However, in the reagent kit for immunoassay, the auxiliary reagent solution is provided as a reagent different from the substrate solution. Accordingly, even if the substrate solution becomes alkaline, the inhibitor of endogenous ALP is not destabilized, and the auxiliary reagent solution can be contained in the reagent under the condition where the inhibitor of endogenous ALP is stable. The reagent kit excellent in storage stability of the inhibitor of endogenous ALP can thereby be provided.

The auxiliary reagent solution is added at the time of the reaction between the ALP label on the solid phase and the substrate. That is, the auxiliary reagent solution unlike a wash fluid is not removed before the solid phase is mixed with the substrate solution, and thus endogenous ALP can be sufficiently inhibited at the time of the reaction between the ALP label and the substrate.

By using the reagent kit for immunoassay comprising such auxiliary reagent solution, accurate immunoassay can be carried out for a long time.

The auxiliary reagent solution is preferably in the form of a solution having the inhibitor of endogenous ALP dissolved in a suitable buffer solution. A buffer agent contained in the auxiliary reagent solution is preferably a buffer agent that can be used at neutral or acidic pH. Specific examples include a phosphate buffer agent, an acetate buffer agent, a citrate buffer agent, MES (2-(N-morpholino) ethanesulfonic acid), PIPES (piperazine-N,N'-bis(2-ethanesulfonic acid), MOPS (3-(N-morpholino) propanesulfonic acid), HEPES (2-[4-(2-hydroxyethyl)-1-piperazinyl]ethanesulfonic acid), Tris (tris (hydroxymethyl) aminomethane) or Tricine (N-[tris(hydroxymethyl)methyl] glycine), TEA (triethanolamine) etc. The buffer agent is preferably a buffer agent not having a buffering ability in the vicinity of alkalinity, and specifically MES can be mentioned.

The concentration of the buffer agent in the auxiliary reagent solution can be suitably selected depending on the type of the buffer agent used. For example, the concentration of the buffer agent in the auxiliary reagent solution is preferably 2 mM to 100 mM, more preferably 3 mM to 50 mM, most preferably 5 mM to 20 mM.

The reaction solution of the ALP label and the substrate contained in the substrate solution also contains the auxiliary reagent solution, and the optimum pH of the ALP is alkaline, and thus this reaction solution is preferably alkaline. Therefore, the pH of the auxiliary reagent solution contained in the reaction solution, the pH of the substrate solution described later, the type of the buffer, the concentration of the buffer agent, etc. in the reagent kit for immunoassay are preferably set such that the reaction solution becomes alkaline.

The substrate solution contains a substrate for ALP. As the substrate, luminescent substrates and coloring substrate for ALP known in the art can be used. Examples of chemiluminescent substrates for ALP include AMPPD (3-(2'-spiroadamantane)-4-methoxy-4-(3"-phosphoryloxy) phenyl-1,2-dioxetane disodium salt), CDP-star™ (disodium 4-chloro-3-(methoxyspiro{1,2-dioxetane-3,2'-(5'-chloro)tricyclo [3.3.1.13,7]decane}-4-yl) phenylphosphate), CSPD™ (disodium 3-(4-methoxyspiro{1,2-dioxetane-3,2-(5'-chloro) tricyclo[3.3.1.13,7]decane}-4-yl) phenylphosphate), etc. Examples of coloring substances for ALP include p-nitrophenyl phosphate, 5-bromo-4-chloro-3-indolyl-phosphoric acid (BCIP), 4-nitro blue tetrazolium chloride (NBT), iodonitrotetrazolium (INT) etc.

When the ALP label is contacted with the above luminescent substrate or coloring substrate, an enzyme reaction is generated and the emission or coloration of a reaction product generated by this reaction is detected, whereby the ALP label can be detected.

The substrate solution is preferably in the form of a solution having the substrate dissolved in a suitable buffer solution. The concentration of the substrate can be suitably selected depending on the type of the substrate. The buffer solution can be suitably selected depending on the type of the substrate, and a buffer solution known in the art can be used.

The optimum pH of the label ALP is alkaline, and thus the substrate solution is preferably alkaline. The pH of the buffer solution is not particularly limited insofar as a reaction solution in which the ALP label is contacted with the substrate has alkaline pH. The pH of the substrate solution is preferably pH 8 to 12, more preferably pH 9 to 11.

As described above, the auxiliary reagent solution can be neutral or acidic. Accordingly, the pH of the reaction solution where the ALP label is contacted with the substrate may be made non-alkaline by the influence of the pH of the auxiliary reagent solution. Therefore, the buffering ability of the substrate solution is preferably made higher than that of the auxiliary reagent solution to reduce the influence of the pH of the auxiliary reagent solution. The method of regulating the buffering abilities of the substrate solution and the auxiliary reagent solution is not particularly limited, and methods known in the art can be used. It is known that generally the buffering ability of a buffer solution is increased as the concentration of its buffer agent is increased. Accordingly, the buffering ability of the substrate solution can be made higher than that of the auxiliary reagent solution by setting the concentration of the buffer agent in the substrate solution higher than in the auxiliary reagent solution. The concentration of the buffer agent can be suitably selected depending on the type of the buffer agent used. For example, the concentration of the buffer agent in the substrate solution is set preferably at least twice, more preferably 5 to 20 times, most preferably 8 to 15 times, as high as the concentration of the buffer agent in the auxiliary reagent solution. Specifically, the concentration of the buffer agent in the substrate solution is preferably 4 mM to 1000 mM, more preferably 10 mM to 500 mM, most preferably 50 mM to 200 mM.

As the buffer agent contained in the auxiliary reagent solution, a buffer agent not having a buffering ability in the vicinity of alkalinity can be used to make the buffering ability of the substrate solution higher than that of the auxiliary reagent solution.

The buffer agent contained in the substrate solution is preferably a buffer agent that can be used under alkaline conditions. Specific examples include glycine, tris (hydroxyethyl) aminoethane (TRIS), ethyl aminoethanol (EAE), diethanolamine (DEA) and 2-amino-2-methyl-1-propanol (AMP). Among these buffer agents, DEA and AMP having their buffering ability at the optimum pH of ALP are preferable.

The reagent kit for immunoassay is a reagent kit in immunoassay using ALP as a label, which is particularly used in immunoassay using a solid phase. Such immunoassay is not particularly limited insofar as ALP is used as a label. Specific examples include EIA, ELISA etc.

The solid phase is not particularly limited insofar as it is a solid phase used in usual immunoassay. The material of the solid phase includes, for example, polymer materials such as latex, rubber, polyethylene, polypropylene, polystyrene, a styrene-butadiene copolymer, polyvinyl chloride, polyvinyl acetate, polyacrylamide, polymethacrylate, a styrene-methacrylate copolymer, polyglycidyl methacrylate, an acrolein-ethylene glycol dimethacrylate copolymer, polyvinylidene difluoride (PVDF) and silicone; agarose; gelatin; erythrocytes; and inorganic materials such as silica gel, glass, inert alumina, and magnetic body. These materials may be used alone or as a mixture of two or more thereof.

The shape of the solid phase is not particularly limited insofar as it is in the form of a usual solid phase used in immunoassay, and examples include a microtiter plate, a test tube, beads, particles, nanoparticles etc. The particles include magnetic particles, hydrophobic particles such as polystyrene latex, copolymer latex particles having hydrophilic groups such as an amino group and a carboxyl group thereon, erythrocytes, gelatin particles etc. From the viewpoint of automatic measurement, the solid phase is preferably magnetic particles, latex particles etc., among which magnetic particles are more preferable.

The magnetic particles are particles containing a magnetic material as the base material. Such magnetic particles are known in the art and include, for example, particles using $Fe_2O_3$ and/or $Fe_3O_4$, cobalt, nickel, ferrite and magnetite as the base material. For the purpose of binding a protein etc. onto the surfaces of magnetic particles, the base material is preferably coated thereon with a polymer etc.

Figure 1:
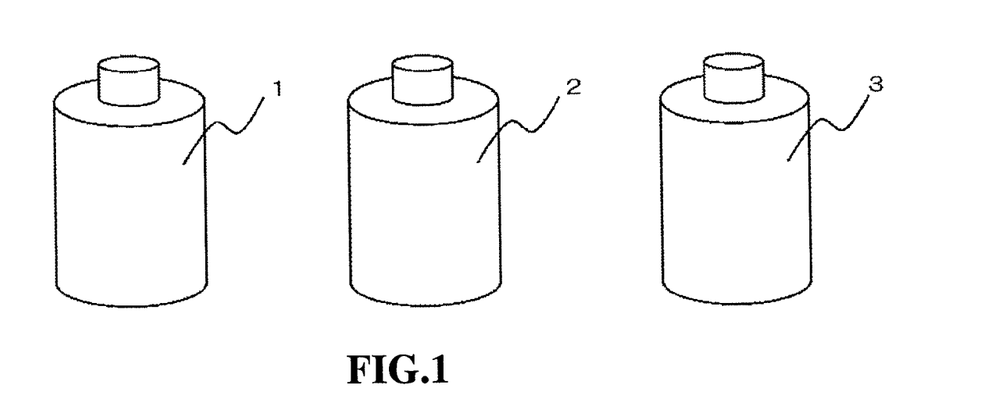
FIG. 1 is a schematic diagram showing one embodiment of the reagent kit for immunoassay in the present invention.

The ALP-labeling substance, the substrate solution and the auxiliary reagent solution are separately packaged respectively in the reagent kit for immunoassay. FIG. 1 shows one example of the reagent kit where the ALP-labeling substance, the substrate solution and the auxiliary reagent solution are in the form of solutions. In FIG. 1, the ALP-labeling substance is accommodated in a first reagent container 1, the substrate solution is accommodated in a second reagent container 2, and the auxiliary reagent solution is accommodated in a third reagent container 3. The reagent kit for immunoassay may be provided if desired with another reagent accommodated in another reagent container. Further, the reagent kit for immunoassay may further be provided with one or more buffer solutions for diluting one or more reagents, instructions for use, and a container usable in the reaction.

The reagent kit for immunoassay may be formed together with other reagents which is used for immunoassay using a solid phase.

Specifically, the reagent kit for immunoassay may be formed by containing:

a first binding substance capable of binding to a measurement substance by antigen-antibody reaction, a solid phase for supporting a complex containing the measurement substance and the first binding substance, an alkaline phosphatase (ALP) labeling substance capable of binding to the measurement substance of the complex, a substrate solution containing a substrate for ALP, and an auxiliary reagent solution containing an inhibitor for inhibiting an endogenous ALP and which is added to the time of reaction between ALP of the ALP-labeling substance bound to the measurement substance of the complex and the substrate.

The reagent kit for immunoassay may be formed by containing:

an alkaline phosphatase (ALP) labeling substance;

a first binding substance capable of binding to a measurement substance and the ALP-labeling substance by antigen-antibody reaction;

solid phase for supporting a first binding substance;

substrate solution containing a substrate for ALP; and an auxiliary reagent solution containing an inhibitor for inhibiting an endogenous ALP and which is added to the time of reaction between ALP of the ALP-labeling substance bound to the first binding substance and the substrate.

The first binding substance may be the one described above. In the reagent kit for immunoassay, the first binding substance may be in the form of a liquid or in the form of a solid to be dissolved in a suitable solvent (for example, water, a buffer solution etc.) just before use.

From the view point of ease in using and handling the reagent kit, the first binding solution is preferably in the form of a liquid dissolved in a solvent. As the buffer solution, a buffer solution used usually in immunoassay can be used and includes, for example, PIPES, TEA, Tris, MES, a phosphate buffer solution, etc.

The solid phase used may be the same solid phase as described above. In the reagent kit for immunoassay, the solid phase may be in a form suspended or contacted with a liquid or in a solid form to be suspended or contacted, just before use, with a suitable solvent (for example, water and a buffer solution). From the viewpoint of ease in using and handling the reagent kit, the solid phase is preferably in a form suspended or contacted with a solvent. As the buffer solution, a buffer solution usually used in immunoassay can be used and includes, for example, PIPES, TEA, Tris, MES, a phosphate buffer solution, etc.

In the reagent kit for immunoassay, the first binding substance may or may not be immobilized on a solid phase.

When the first binding substance has been immobilized on a solid phase, the reagent kit for immunoassay contains, for example, a reagent containing the solid phase on which the first binding substance has been immobilized, an ALP-labeling substance, a substrate solution, and an auxiliary reagent solution. In case of an immunoassay using this reagent kit, the order of mixing a sample, a reagent containing the solid phase on which the first binding substance has been immobilized, and an ALP-labeling substance is not particularly limited.

One example of an immunoassay using this reagent kit is described as following. First, a sample is mixed with the reagent containing the solid phase, whereby a complex containing the measurement substance and the first binding substance is formed on the solid phase. Then, the solid phase on which the complex has been supported and the ALP-labeling substance are mixed with each other, whereby the ALP-labeling substance is bound to the complex on the solid phase. Then, the auxiliary reagent solution and the substrate solution are added to the solid phase on which the ALP-labeling substance-bound complex has been supported, and the ALP label on the solid phase and the substrate contained in the substrate solution are reacted with each other in the presence of the auxiliary reagent solution containing an inhibitor of endogenous ALP. In the solution where the ALP label is contacted with the substrate, the enzyme reaction of the ALP label with the substrate can thereby be generated while endogenous ALP derived from the sample is effectively inhibited. Then, the light emission or coloration of a reaction product generated by the enzyme reaction of the ALP label with the substrate is detected, whereby the measurement substance can be accurately measured.

The method of immobilizing the first binding substance on the solid phase is known. This immobilization can be carried out for example with physical adsorption method, covalent bonding method, ionic bonding method, or a combination thereof.

The first binding substance can be immobilized on the solid phase via a bond between biotin and avidin or the like. The combination of substances via which the first binding substance is immobilized on the solid phase includes not only biotin and avidin or the like, but a hapten and an anti-hapten antibody, nickel and a histidine tag, or glutathione and glutathione-S-transferase. The hapten and anti-hapten antibody include, for example, DNP and an anti-DNP antibody.

In this specification, the phrase "avidin or the like" is intended to encompass avidin and streptavidin.

When the first binding substance is not immobilized on a solid phase, the reagent kit for immunoassay contains, for example, a reagent containing the first binding substance, a reagent containing a solid phase, an ALP-labeling substance, a substrate solution and an auxiliary reagent solution. In case of an immunoassay using this reagent kit, the order of mixing a sample, a reagent containing the first binding substance, a reagent containing the solid phase, and an ALP-labeling substance is not particularly limited.

One example of an immunoassay using this reagent kit is described as following. First, a sample is mixed with the reagent containing the first binding substance, whereby a complex containing the measurement substance and the first binding substance is formed. Then, this complex is mixed with the reagent containing the solid phase, whereby the complex is supported on the solid phase. Then, the complex-supporting solid phase is mixed with the ALP-labeling substance, whereby the ALP-labeling substance is bound to the complex. Then, the auxiliary reagent solution and the substrate solution are added to the solid phase on which the ALP-labeling substance-bound complex has been supported, and the ALP label on the solid phase and the substrate contained in the substrate solution are reacted with each other in the presence of the auxiliary reagent solution containing an inhibitor of endogenous ALP. In the solution where the ALP label is contacted with the substrate, the enzyme reaction of the ALP label with the substrate can thereby be generated while endogenous ALP derived from the sample is effectively inhibited. Then, the light emission or coloration of a reaction product generated by the enzyme reaction of the ALP label with the substrate is detected, whereby the measurement substance can be accurately measured.

When this reagent kit is used for an immunoassay using competitive method, there can be a case of adding the ALP-labeling substance after mixing a sample, the reagent containing the first binding substance, and the reagent containing the solid phase, and another case of adding the reagent containing the solid phase after mixing a sample, the reagent containing the first binding substance, and the ALP-labeling substance.

It is preferable that when the first binding substance is not immobilized on the solid phase, a solid phase-binding site has been added to the first binding substance, and a third binding substance capable of binding to the solid phase-binding site has been immobilized on the solid phase. A complex containing the measurement substance and the first binding substance can thereby be formed on the solid phase.

The solid phase-binding site and the third binding substance are not particularly limited insofar as they are a combination of substances which can be bound specifically to each other when contacted under the conditions where the reagent kit is used. Such combination includes, for example, biotin and avidin or the like, a hapten and an anti-hapten antibody, nickel and a histidine tag, or glutathione and glutathione-S-transferase. The hapten and anti-hapten antibody include, for example, DNP and an anti-DNP antibody. A combination of biotin and avidin or the like is preferable. More preferably, the solid phase-binding site includes biotin and the third binding substance is avidin or the like. In substances as the combination of the solid phase-binding site and the third binding substance, the substance immobilized on the solid phase is not limited, and either may be immobilized on particles as the solid phase.

When the third binding substance is avidin or the like, avidin or the like can be immobilized on a solid phase by binding avidin or the like to a solid phase to which a substance (e.g. biotin) capable of binding to avidin or the like has been bound. Alternatively, avidin or the like can be immobilized on a solid phase by a method described in JP-A 2006-226689.

The solid phase to which avidin or the like was bound can be purchased from, for example, JSR Co., Ltd. or Dynal Biotech.

In the case of the competitive method, an ALP-labeling substance binding to the free first binding substance on a solid phase is used.

For example, when the solid phase is particles while a particle dispersion is used as the auxiliary reagent solution, the particles on which the ALP-labeling substance-bound complex has been supported are dispersed in the particle dispersion, and the substrate solution is added thereto.

Immunoassay Method

The reagent kit for immunoassay can be utilized in an immunoassay method. Such immunoassay method is An immunoassay method comprising: forming, on a solid phase, a complex comprising a measurement substance in a sample, an alkaline phosphatase (ALP) labeling substance capable of binding to the measurement substance, and a first binding substance which is capable of binding to the measurement substance by antigen-antibody reaction and is capable of binding to the solid phase; reacting ALP in the ALP-labeling substance bound to the measurement substance in the complex, with a substrate for ALP contained in a substrate solution, in the presence of an auxiliary reagent solution comprising an inhibitor for inhibiting an endogenous ALP; and detecting a reaction product produced by the reaction between ALP and the substrate.

Such immunoassay method is An immunoassay method comprising: mixing a sample, an alkaline phosphatase (ALP) labeling substance, a first binding substance capable of binding to the ALP-labeling substance and a measurement substance in the sample by antigen-antibody reaction, and a solid phase for supporting the first binding substance; reacting ALP of the ALP-labeling substance bound to the first binding substance supported by a solid phase, with a substrate for ALP contained in a substrate solution, in the presence of an auxiliary reagent solution comprising an inhibitor for inhibiting an endogenous ALP; and detecting a reaction product produced by the reaction between ALP and the substrate.

The step of forming, on a solid phase, a complex comprising a measurement substance in a sample, an alkaline phosphatase (ALP) labeling substance capable of binding to the measurement substance, and a first binding substance capable of binding to the measurement substance by antigen-antibody reaction and is capable of binding to the solid phase, can be carried out by mixing the measurement substance in a sample, ALP-labeling substance, and a solid phase. Method for mixing the measurement substance in a sample, ALP-labeling substance, and a solid phase can be the same method as described in the reagent kit for immunoassay.

The step of mixing a sample, an alkaline phosphatase (ALP) labeling substance, a first binding substance capable of binding to the ALP-labeling substance and the measurement substance in a sample by antigen-antibody reaction, and a solid phase for supporting the first binding substance, can be carried out by the method as described in the reagent kit for immunoassay using competitive method.

As described in the reagent kit for immunoassay, the first binding substance may or may not be immobilized on a solid phase.

The measurement substance is not particularly limited insofar as generally its presence can be detected or its amount can be quantified by immunoassay. Examples include proteins, sugars, lipoproteins and hormones. Examples of such measurement substances include human immunodeficiency virus (HIV) and antibodies thereto, human T lymphotropic virus type 1 (HTLV-1) and antibodies thereto, hepatitis C virus (HCV) and antibodies thereto, hepatitis B virus (HBV) and antibodies thereto, carcinoembryonic antigen (CEA), C-reactive protein (CRP), *Treponema pallidum* (TP) antibody, α1-antitrypsin, α1-microglobulin, β2-microglobulin, haptoglobin, transferrin, ceruloplasmin, ferritin, albumin, hemoglobinA1, hemoglobinA1C, myoglobin, myosin, dupan-2, α-fetoprotein (AFP), tissue polypeptide antigen (TPA), apolipoprotein A1, apolipoprotein E, rheumatoid factor, anti-streptolysin O (ASO), antithrombin III (AT-III), a plasmin/α2 plasmin inhibitor complex (PIC), a thrombin/anti-thrombin III complex (TAT), thrombomodulin (TM), a tissue plasminogen activator/plasminogen activator inhibitor I complex (tPAI.C), thyroid hormones (thyroxine (T3), free thyroxine (FT3), triode thyronine (T4), free triode thyronine (FT4)), thyroid stimulating hormone (TSH), luteinizing hormone (LH), follicle-stimulating hormone (FSH), cortisol, insulin etc.

A sample containing the measurement substance includes samples such as blood, plasma, serum and urine as well as samples obtained by pretreatment of the above samples. The pretreatment includes, for example, insolubles removal techniques such as centrifugation and filtration.

The antigen or antibody binding specifically to the measurement substance can be the same as described in the reagent kit for immunoassay. Particles as the solid phase can be the same as described in the reagent kit for immunoassay.

In the immunoassay method described above, the step in which ALP in the ALP-labeling substance bound to the measurement substance of the complex is reacted with a substrate for ALP contained in the substrate solution, in the presence of the auxiliary reagent solution containing an inhibitor of endogenous ALP, can be carried out by the method described in the reagent kit for immunoassay as described above.

In the immunoassay using the competitive method described above, the step in which ALP in the ALP-labeling substance bound to the first binding substance supported on the solid phase is reacted with a substrate for ALP contained in the substrate solution, in the presence of the auxiliary reagent solution containing an inhibitor of endogenous ALP, can be carried out by the method described in the reagent kit for immunoassay as described above.

By this step, the enzyme reaction of the ALP label with the substrate can be generated in the solution where the ALP label is contacted with the substrate, while endogenous ALP derived from the sample is effectively inhibited. Then, the light emission or coloration of a reaction product generated by the enzyme reaction of the ALP label with the substrate is detected, whereby the measurement substance can be accurately measured.

The step of detecting the reaction product produced by the reaction between ALP and the substrate can be carried out by utilizing a method known in the art. The reaction product can be detected by measuring a light or a color generated from the reaction product with a suitable apparatus. The apparatus includes a spectrophotometer, a luminometer etc.

EXAMPLES

Hereinafter, the present invention will be described in more detail by reference to the Examples. The present invention is not limited to these examples.

The reagents used in the Examples are as follows:

(1) Preparation of an HBs Antibody Reagent

Antibody 1053 produced by hybridoma HBs-1053 described in JP-A 2006-321746 was used as HBs antibody. Then, this HBs antibody was biotinylated with Biotinylation Kit (Sulfo-OSu) (DOJINDO LABORATORIES). The resulting biotinylated HBs antibody was dissolved at a final concentration of 1.0 μg/mL in 0.1 M MES buffer solution, pH 6.5 and used as HBs antibody reagent.

The hybridoma HBs-1053 was internationally deposited by Sysmex Corporation and assigned International Deposition No. FERM BP-10582.

(2) Preparation of a Magnetic Particle Reagent

Commercial streptavidin-coated magnetic particles (referred to hereinafter as "ST magnetic particles") were dissolved at a final density of 1% in 20 mM MES buffer solution, pH 6.5 and used as a magnetic particle reagent.

(3) Preparation of an ALP-Labeling HBs Antibody Reagent

Antibody 149 produced by hybridoma HBs-149 described in JP-A 2006-321746 was used as HBs antibody. Then, this HBs antibody was labeled with ALP by using EMCS (DOJINDO LABORATORIES). The resulting ALP-labeling antibody was dissolved at a final concentration of 0.3 U/mL in 0.1 M MES buffer solution, pH 6.5 and used as ALP-labeling HBs antibody reagent.

The hybridoma HBs-149 was internationally deposited by Sysmex Corporation and assigned International Deposition No. FERM BP-10583.

(4) Preparation of a Particle Dispersion

A levamisole-containing particle dispersion was prepared as an inhibitor of endogenous ALP. The composition of the particle dispersion is as follows:
10 mM MES buffer solution, pH 6.5
1 mM or 2 mM levamisole hydrochloride (Tokyo Kasei Kogyo Co., Ltd.)

(5) Substrate Solution
CDP-star T (Applied Biosystems)

Reference Example 1

In this example, the storage stability of the inhibitor of endogenous ALP contained in the particle dispersion prepared in (4) above was examined. The concentration of levamisole in the particle dispersion used in this example was 1 mM.

Specifically, the following accelerated test was carried out by using the particle dispersion described above. In the accelerated test, the particle dispersion was introduced into a 50-mL container (material: polypropylene) and left in the dark at 55° C. for 6 days. Then, after standing, the particle dispersion in the container was returned to room temperature and then transferred from the container to a spectrophotometric cell to confirm whether precipitation had occurred or not.

For comparison, a reagent (Comparative Reagent 1) having levamisole mixed in a high pH amine buffer solution described in JP-A 2-207800 was used. A kit for immunoassay with ALP is described in JP-A 2-207800, and it is described therein that levamisole can be stabilized even at high pH by incorporating a specific amine such as 2-amino-2-methyl-1-propanol together with the inhibitor of endogenous ALP.

The composition of Comparative Reagent 1 is as shown below. The experimental method is the same as described above except that Comparative Reagent 1 was used in place of the particle dispersion.

The composition of Comparative Reagent 1:
0.1 M AMP buffer solution, pH 9.6
1 mM levamisole hydrochloride (Tokyo Kasei Co., Ltd.)

Figure 2:
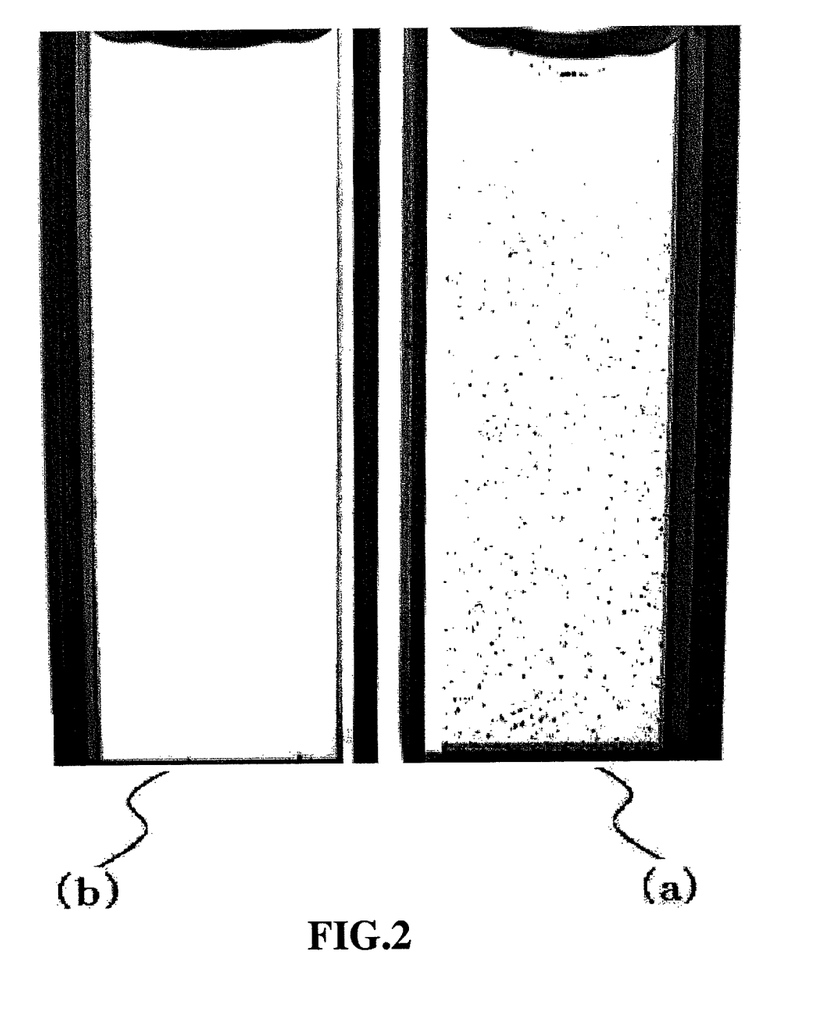
FIG. 2 shows a photograph (a) of a side of a spectrophotometric cell into which Comparative Reagent 1 after an accelerated test was introduced and a photograph (b) of a side of a spectrophotometric cell into which a particle dispersion after an accelerated test was introduced.

The experimental results are shown in FIG. 2. FIG. 2 is a photograph of a side of the spectrophotometric cell to which each reagent after the accelerated test was added. FIG. 2 (a) shows the result where the particle dispersion was used, and FIG. 2 (b) shows the result where Comparative Reagent 1 was used.

As described above, Comparative Reagent 1 is a reagent using, as a buffer, a high pH amine buffer solution described in JP-A 2-207800. In JP-A 2-207800, it is described that in a specific high pH amine buffer solution such as AMP, levamisole is stable even under alkaline conditions. From the result in FIG. 2 (b), however, precipitates were confirmed in the solution with Comparative Reagent 1. By analysis, these precipitates were found to be precipitates derived from levamisole (data are not shown). It was thereby found that levamisole is poor in storage stability with Comparative Reagent 1.

From the result in FIG. 2 (a), on the other hand, precipitates were not confirmed in the particle dispersion. From the foregoing, it was found that the storage stability of the inhibitor of endogenous ALP is excellent in the particle dispersion.

Example 1

In this example, the effect of the inhibitor of endogenous ALP contained in the particle dispersion prepared in (4) above on reduction of the influence of endogenous ALP was examined. The concentration of levamisole in the particle dispersion used in this example was 2 mM.

Specifically, the reagents prepared in (1) to (5) above were used and the luminescence intensities of HBs antigen-negative samples were measured. The measurement method is described below.

First, 25 μL sample was mixed with 30 μL of the HBs antibody reagent and then incubated at 42° C. for about 3 minutes, whereby an HBs antigen in the sample was reacted with the biotinylated HBs antibody in the HBs antibody reagent. Subsequently, 30 μL of the magnetic particle reagent was added to the mixture and then incubated for about 2 minutes, and a complex consisting of the HBs antigen and the biotinylated HBs antibody was immobilized on the ST magnetic particles. The ST magnetic particles were washed 3 times with about 150 μL wash fluid (0.1% Tween 20, 20 mM sodium phosphate buffer solution, pH 7.5), and then 100 μL of the ALP-labeling HBs antibody reagent was added to the ST magnetic particles from which the wash fluid had been removed. The mixture was then incubated at 42° C. for 3 minutes, and the ALP-labeling HBs antibody was bound to the complex on the ST magnetic particles. The ST magnetic particles were washed 3 times with 150 μL of the wash fluid. 50 μL of the particle dispersion was added to the ST magnetic particles from which the wash fluid had been removed, then the ST magnetic particles were dispersed in the particle dispersion, 100 μL of the substrate solution was added thereto, and the luminescence intensity of the sample was measured with LUMI-COUNTER 700 (Microtec Nichion).

As samples, 41 kinds of HBs antigen-negative sera (negative sera 1 to 41) were used. As a negative control, 0.1 M TEA buffer solution containing BSA (5% BSA, pH 7.0) was used in measurement. As a positive control, HBs antigen-positive serum was used in measurement. The results are shown in Tables 1 and 2.

For comparison, 10 mM MES buffer solution, pH 6.5 (Comparative Reagent 2) not containing levamisole was used in measurement in place of the levamisole-containing particle dispersion. The measurement method is the same as described above except that Comparative Reagent 2 was used in place of the particle dispersion described above. The results are shown in Tables 1 and 2.

TABLE 1

| Sample | | Without Levamisole (Luminescence Intensity, Counts) | With Levamisole (Luminescence Intensity, Counts) |
|---|---|---|---|
| NC | | 886 | 705 |
| PC | | 268288 | 258759 |
| Negative Sera | 1 | 1252 | 849 |
| | 2 | 1079 | 803 |
| | 3 | 1079 | 793 |
| | 4 | 997 | 789 |
| | 5 | 1811 | 938 |
| | 6 | 1065 | 737 |
| | 7 | 1171 | 773 |
| | 8 | 1360 | 794 |
| | 9 | 994 | 782 |
| | 10 | 2689 | 1006 |
| | 11 | 1042 | 894 |
| | 12 | 1274 | 859 |
| | 13 | 1022 | 798 |
| | 14 | 1109 | 900 |
| | 15 | 1253 | 843 |
| | 16 | 1037 | 976 |
| | 17 | 1775 | 1066 |
| | 18 | 1121 | 915 |
| | 19 | 1685 | 937 |
| | 20 | 1553 | 945 |

TABLE 2

| Sample | | Without Levamisole (Luminescence Intensity, Counts) | With Levamisole (Luminescence Intensity, Counts) |
|---|---|---|---|
| Negative Sera | 21 | 1198 | 847 |
| | 22 | 1082 | 893 |
| | 23 | 1723 | 973 |
| | 24 | 1067 | 758 |
| | 25 | 1202 | 833 |
| | 26 | 1053 | 844 |
| | 27 | 1407 | 945 |
| | 28 | 1123 | 904 |
| | 29 | 1065 | 813 |
| | 30 | 1135 | 840 |
| | 31 | 1225 | 1076 |
| | 32 | 1240 | 1016 |
| | 33 | 1066 | 912 |
| | 34 | 1113 | 1172 |
| | 35 | 1057 | 793 |
| | 36 | 1076 | 844 |
| | 37 | 1216 | 821 |
| | 38 | 1023 | 931 |
| | 39 | 1007 | 1042 |
| | 40 | 1146 | 808 |
| | 41 | 1004 | 885 |

In the tables, "NP" is a negative control, and "PC" is a positive control. The item "With Levamisole" shows fluorescence intensity (counts) obtained in measurement using a levamisole-containing particle dispersion. The item "Without Levamisole" shows fluorescence intensity (counts) obtained in measurement using levamisole-free Comparative Reagent 2.

Figure 3:
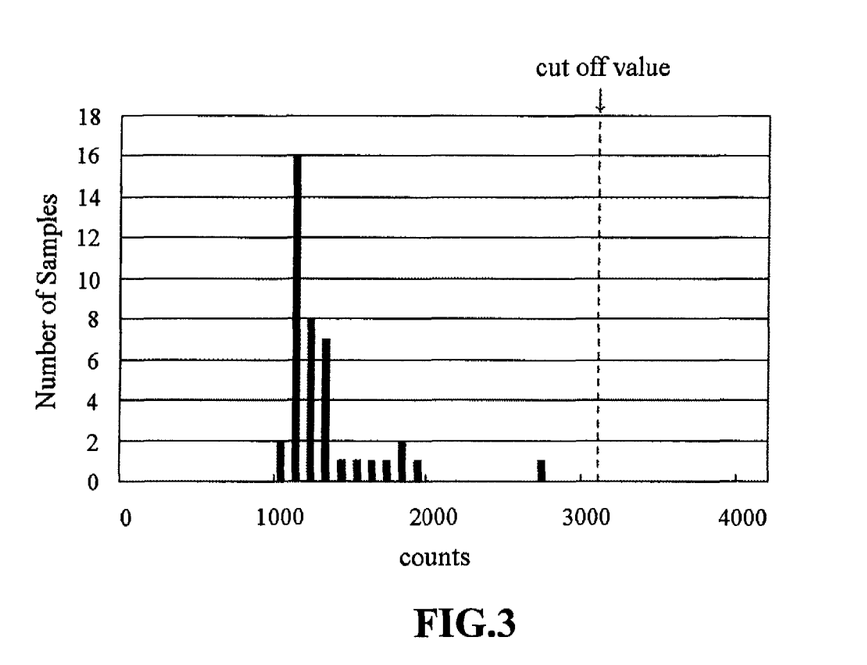
FIG. 3 is a distribution chart (histogram) showing the distributed state of each negative sample when Comparative Reagent 2 was used in the Examples.
Figure 4:
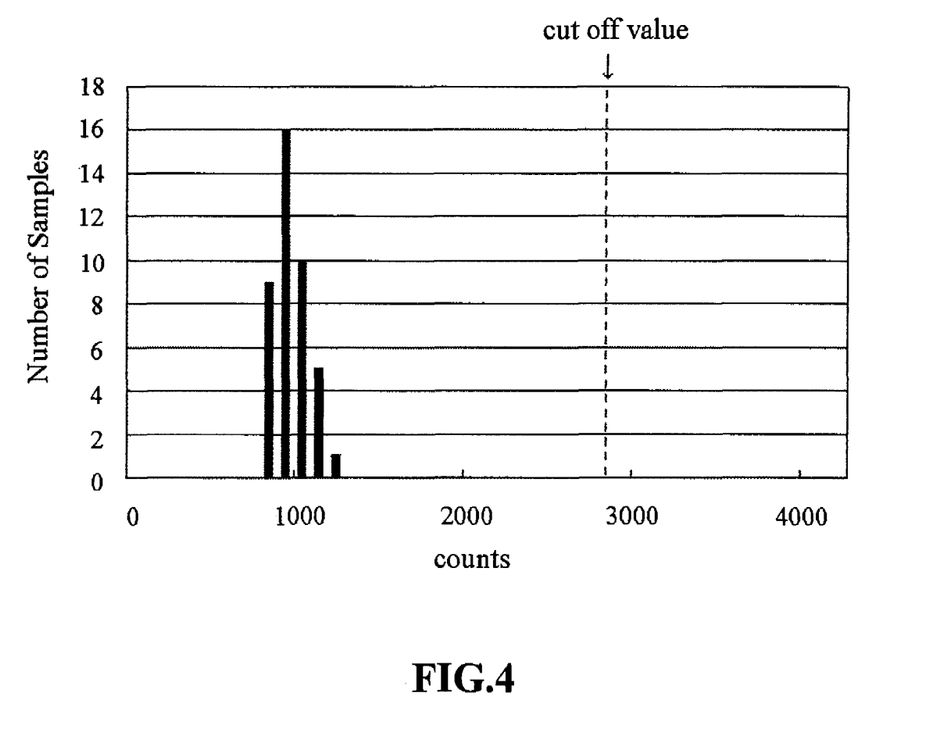
FIG. 4 is a distribution chart (histogram) showing the distributed state of each negative sample when a particle dispersion was used in the Examples.

FIGS. 3 and 4 are distribution charts (histograms) showing the distributed state of the negative samples relative to fluorescence intensity (counts). In these distribution charts, counts in each of sections divided per 100 counts are shown on the abscissa, and the number of samples contained in each section is shown on the ordinate. The counts at which HBsAg became 0.03 U/mL was determined as cutoff value. The cutoff value in FIG. 3 is 3092, and the cutoff value in FIG. 4 was 2855. A sample showing a value higher than the cutoff value can be judged to be positive, while a sample showing a value lower than the cutoff value can be judged to be negative. FIG. 3 shows the results where levamisole-free Comparative Reagent 2 was used, and this histogram was prepared on the basis of fluorescence intensity (counts) in the item "Without Levamisole" in Tables 1 and 2. FIG. 4 shows the results where the levamisole-containing particle dispersion was used, and this histogram was prepared on the basis of fluorescence intensity (counts) in the item "With Levamisole" in Tables 1 and 2.

From the results of Tables 3 and 4, variation of fluorescence intensities obtained from negative samples is decreased by using the levamisole-containing particle dispersion, and the counts of all negative samples used in the measurement were about 800 to 1300. Particularly with respect to negative samples showing relatively high counts (about 1500 to 2700), their counts are decreased in FIG. 4, and their distribution is shifted to lower counts. This indicates that these negative samples are samples influenced relatively highly by an endogenous ALP. It was found that the levamisole-containing particle dispersion can be used to inhibit the endogenous ALP in such samples, thereby effectively eliminating the influence of the endogenous ALP. With respect to negative samples showing counts in the vicinity of the cutoff value in FIG. 3, their counts are decreased in FIG. 4, and their distribution is shifted to lower counts. It was thereby found that the levamisole-containing particle dispersion can be used to eliminate the influence of an endogenous ALP effectively, thereby preventing occurrence of false positive.

From the foregoing, it was found that in the auxiliary reagent solution containing an inhibitor of endogenous ALP, the inhibitor of endogenous ALP is excellent in storage stability, and by using a reagent kit containing this auxiliary reagent solution, an endogenous ALP can be effectively inhibited to give highly accurately measurement results.

For example, use of the auxiliary reagent solution containing an inhibitor of endogenous ALP is advantageous over use of a wash fluid containing an inhibitor of endogenous ALP in that the inhibitor of endogenous ALP can be present in a necessary amount in a reaction solution of the enzyme reaction of the ALP label with its substrate. Further, in the immunoassay using particles as a solid phase and the auxiliary reagent solution as a particle dispersion, the amount of a wash fluid used may be larger than the amount of the particle dispersion used in one measurement. In the Examples above, for example, the amount of the particle dispersion is 50 μL while the amount of the wash fluid is about 900 μL in one measurement. Thus, the cost involved in the inhibitor of endogenous ALP can be more reduced by using the auxiliary reagent solution (particle dispersion) containing the inhibitor of endogenous ALP than by using the wash fluid containing the inhibitor of endogenous ALP.

What is claimed is:

1. An immunoassay method comprising:
    forming, on a solid phase, a complex comprising a measurement substance in a sample, an alkaline phosphatase (ALP) labeling substance capable of binding to the measurement substance, and a first binding substance which is capable of binding to the measurement substance by antigen-antibody reaction and is capable of binding to the solid phase;
    contacting the complex bound to the solid phase, after said forming step, with an auxiliary reagent solution having a pH value of 4-7 comprising an inhibitor for inhibiting an endogenous ALP, wherein the inhibitor is selected from the group consisting of levamisole, homologues of levamisole whose phenyl ring is substituted with a C1 to C6 lower alkyl group, homologues of levamisole whose phenyl ring is substituted with a halogen atom, and tetramisole;
    reacting ALP in the ALP-labeling substance bound to the measurement substance in the complex, after said contacting step, with a substrate for ALP contained in a substrate solution having a pH value of 9-11, in the presence of the auxiliary reagent solution to form a mixture; and
    detecting, after said reacting step, a reaction product produced by the reaction between ALP and the substrate,
    wherein each of the substrate solution and the auxiliary reagent solution comprise a buffer agent, and the substrate solution has a higher buffering ability than that of the auxiliary reagent solution, and
    wherein the substrate solution is accommodated in a first reagent container, and the auxiliary reagent solution is accommodated in a second reagent container different from the first reagent container.

2. The method of claim 1, wherein the mixture obtained by implementing the reaction step is alkaline.

3. The method of claim 1, wherein the inhibitor is levamisole.

4. The method of claim 1, wherein ALP in the ALP-labeling substance is selected from the group consisting of bacterium-derived ALP and intestine-derived ALP.

5. The method of claim 1, wherein the auxiliary reagent solution has a pH value of 6 to 7.

6. The method of claim 1, wherein the concentration of the buffer agent in the substrate solution is 5 to 20 times as high as that of the concentration of the buffer agent in the auxiliary reagent solution.

7. The method of claim 1, wherein the substrate is a luminescent substrate.

8. The method of claim 7, wherein the luminescent substrate is disodium 4-chloro-3-(methoxyspiro{1,2-dioxetane-3,2'-(5'-chloro)tricyclo[3.3.1.13.7]decane}-4-yl)phenylphosphate or disodium 3-(4-methoxyspiro{1,2-dioxetane-3,2-(5'-chloro)tricyclo[3.3.1.13.7]decane}-4-yl) phenylphosphate.

9. The method of claim 1, further comprising washing, after said forming step, the solid phase with wash fluid.

10. The method of claim 9, wherein the wash fluid comprises a surfactant agent.

11. The method of claim 1,
    wherein the solid phase is a particle, and
    the contacting step comprises dispersing the particle.

12. The method of claim 11, wherein the particle is a magnetic particle.

13. The method of claim 11, wherein the auxiliary reagent solution does not comprise a surfactant agent.

* * * * *